United States Patent
Riordan

(10) Patent No.: US 10,729,595 B2
(45) Date of Patent: Aug. 4, 2020

(54) TAMPON

(71) Applicant: Robbin Field Riordan, Alpharetta, GA (US)

(72) Inventor: Robbin Field Riordan, Alpharetta, GA (US)

( * ) Notice: Subject to any disclaimer, the term of this patent is extended or adjusted under 35 U.S.C. 154(b) by 379 days.

(21) Appl. No.: 15/614,523

(22) Filed: Jun. 5, 2017

(65) Prior Publication Data

US 2017/0266060 A1      Sep. 21, 2017

Related U.S. Application Data

(62) Division of application No. 13/411,943, filed on Mar. 5, 2012, now Pat. No. 9,744,081.

(51) Int. Cl.
| | | |
|---|---|---|
| *A61F 13/20* | (2006.01) | |
| *A61F 13/34* | (2006.01) | |
| *B23P 17/04* | (2006.01) | |

(52) U.S. Cl.
CPC ............ *A61F 13/34* (2013.01); *A61F 13/208* (2013.01); *B23P 17/04* (2013.01); *Y10T 29/49826* (2015.01)

(58) Field of Classification Search
CPC ...... A61F 13/20; A61F 13/202; A61F 13/204; A61F 13/206; A61F 13/2062; A61F 13/2065; A61F 13/208; A61F 13/34
See application file for complete search history.

(56) References Cited

U.S. PATENT DOCUMENTS

| | | | | |
|---|---|---|---|---|
| 4,200,101 A | * | 4/1980 | Glassman | A61F 13/2051 604/385.18 |
| 4,222,381 A | * | 9/1980 | Widlund | A61F 13/206 604/365 |
| 4,226,237 A | * | 10/1980 | Levesque | A61F 13/206 604/374 |
| 5,201,326 A | * | 4/1993 | Kubicki | A61K 9/0036 128/832 |
| 5,988,386 A | * | 11/1999 | Morrow | A61F 13/26 206/440 |
| 8,247,638 B2 | * | 8/2012 | Kim | A61F 13/2051 604/361 |
| 2004/0254557 A1 | * | 12/2004 | Kraemer | A61F 13/2051 604/385.18 |

* cited by examiner

*Primary Examiner* — Catharine L Anderson
(74) *Attorney, Agent, or Firm* — Matthew L. Grell; Jeffrey C. Watson; Grell & Watson Patent Attorneys LLC

(57) ABSTRACT

An improved tampon has a tampon body and a removal string, having a length (L) between a first end and second end permanently affixed at or along at least one first end of the string to the tampon body and wherein the second end is looped back into the tampon body and attached thereto to form a shortened single loop. The second end can be permanently attached or removably attached to the tampon body and the single loop extends from the tampon body a distance (D) less than half the length (L) of the removal string.

6 Claims, 4 Drawing Sheets

TAMPON

CROSS-REFERENCE TO RELATED APPLICATIONS

This application is a continuation of and claims benefit to U.S. patent application Ser. No. 13/411,943, filed Mar. 5, 2012, now entitled "IMPROVED TAMPON", which is hereby incorporated by reference in its entirety.

TECHNICAL FIELD

This invention relates to an improved sanitary tampon. More particularly to a tampon with a concealed removal string designed to prevent embarrassing string exposure when wearing the device during activities like swimming. The device allowing the bather to wear swimming apparel without concern for the string being visible.

BACKGROUND OF THE INVENTION

Tampon devices are manufactured to enable a woman to participate in activities such as swimming even during the menstrual cycle.

The old prior art tampons were so water absorbent that menstruating women could not or would not be able to swim as the device would also absorb water and when fully saturated would bleed into the water. Current technology has enabled new tampon construction that has a hydrophilic portion for blood absorption and a hydrophobic portion at the distal or string or cord end to block water absorption and thus are well suited for swimming or spa usages. Even the removal string or cord is made of non-water/fluid wicking hydrophobic material. Therefore it is now accepted and hygienically safe to enjoy swimming during this time.

These tampons have a long string or cord extending from the tampon that facilitates removal. This removal string is exposed and easily observable when a woman is wearing a bathing suit. This is embarrassing as it draws attention to the tampon. To avoid this string exposure the current practice is to cut the extending string portions or ends, which are specifically designed to be exposed to facilitate removal, to shorten them to a length that fits well inside body cavity thus concealing them. Unfortunately most women needing to do this may have no access to scissors or knives to cut the excess string if at the club or public swimming pool. Secondarily, if too much string is removed, there is the risk of needing forceps or other means to grasp the tampon when it must be removed. Accordingly, there is a need to provide a safe, reliable product that solves this issue of tampon string exposure from under swimwear or under garments.

The present invention described below provides a solution to prevent exposed "removal strings" while maintaining the safe, reliable use of the removal string.

SUMMARY OF THE INVENTION

An improved tampon has a tampon body and a removal string, having a length (L) between a first end and second end permanently affixed at or along at least one first end of the string to the tampon body and wherein the second end is looped back into the tampon body and attached thereto to form a shortened single loop. The second end can be permanently attached or removably attached to the tampon body and the single loop extends from the tampon body less than half the length of the removal string.

The second end can be releasably attached to the tampon body and can be detached from the tampon body to facilitate removal allowing the removal string to be extended to a full removal length. The second end when detached allows the removal string to extend from the tampon body a distance equal to an at least industry standard minimum length of at least 4 inches (10.2 cm). The removal string first and second ends when attached to the tampon body form the single loop in a one piece knotless loop. At least one first end is sewn, hot welded, bonded, adhesively glued or otherwise permanently affixed to the tampon body. Preferably, the removal string is made of a hydrophobic material to prevent water or blood absorption and the tampon body has an upper portion made of a hydrophilic material for improved blood absorption and a lower portion of a water blocking hydrophobic material.

BRIEF DESCRIPTION OF THE DRAWINGS

The invention will be described by way of example and with reference to the accompanying drawings in which.

DETAILED DESCRIPTION OF THE INVENTION

Figure 1:
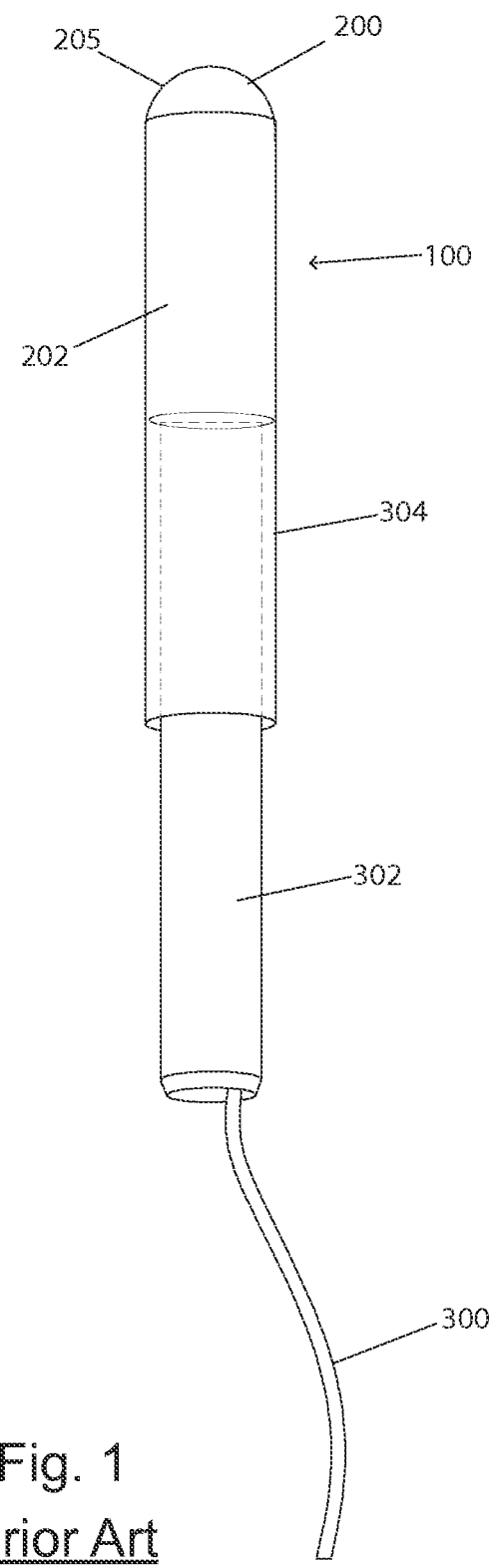
FIG. 1 is a plan view of a conventional prior art tampon assembly with an inner applicator tube and an outer applicator tube shown with a tampon stowed inside the outer applicator tube and the removal string extending outwardly from the inner tube of the tampon assembly.

With reference to FIG. 1 there is shown a plan view of a conventional prior art tampon assembly 100 with an inner applicator tube 302 and an outer applicator tube 304 shown with the tampon 200 stowed within the outer applicator tube 304 and a removal string 300 extending outwardly from the inner tube 302 of the tampon assembly 100. These prior art tampons can come in a variety of sizes and are sold having different absorbency ratings and packaging. Generally, the outward appearance of a tampon is similar for almost all commercially sold brands, but their absorbency does vary. All tampons have a cord or string for removal and some have an additional outer cover to aid in insertion and withdrawal. Many women prefer the use of a tampon that is contained within an applicator to further aid insertion. The prior art tampon shown in FIG. 1 employs an applicator 302, 304. The tampon, when sold as an assembly 100 of the tampon 200 and the applicator 302, 304, facilitates insertion of the tampon 200 into the vagina without the requirement of touching the tampon 200 during insertion.

Many tampons, alternatively commonly referred to as digital or non-applicator tampons are sold without applicators. These are simply unwrapped from their packaging and simply pushed into the vagina with fingers. These tampons can range in size from 1.5 to 4.5 inches.

Tampon applicators may be made of plastic or cardboard and are of a similar design to a syringe. The applicator consists of two tubes, an outer or barrel 304 and an inner or plunger 302. The outer tube 304 has a smooth surface to aid insertion and sometimes comes with a rounded end that is petaled. As shown in FIG. 1, the tampon 200 is actually extending slightly outwardly from the outer tube 304. The tampon 200 itself sits inside the outer tube 304 near the open end as shown partially exposed out of the outer open end of the outer tube 304. The inner tube 302 is encased inside the outer tube 304 and is held in place by a locking mechanism or simply friction. The outer tube 304 is inserted into the vagina and the inner tube 302 is pushed into the outer tube 304 typically using a finger pushing the tampon 200 through and into the vagina. In this fashion the tampon 200 can be placed without ever touching that area of the body. Once fully inserted, the applicator 302, 304 is removed and the dangling string or cord 300 is exposed hanging from the vagina. Typically these strings 300 extend at least 4 inches and sometimes up to six inched beyond the distal end of the tampon.

In the United States, a tampon is considered a class 2 medical device. The majority of tampons sold in the United States are made of rayon or a blend of rayon and cotton. Organic cotton compounds are made from only 100 percent cotton. Tampons are sold individually wrapped to keep them clean. Since the vagina is not a sterile body cavity, and for the most part contains good bacteria, there is no need for any menstrual device to be sterilized. While the materials for use in a tampon can vary, certain treatments can be used to facilitate either the absorbency or the lack of absorbency of the material, it is important to note that the tampons should be safe from any toxic material such as pesticides or chlorine. Such chemicals can add to health concerns. It is recommended by the US FDA that certain guidelines be followed when using tampons to avoid Toxic Shock Syndrome. One is that the woman chooses the lowest absorbency needed for one's flow or bleeding condition, consider using cotton or cloth tampons rather than rayon and change the tampons every 4 to 6 hours. It is often advised that a woman alternate between tampons and pads and to avoid tampon usage overnight or when sleeping. Increased awareness of warning signs of Toxic Shock Syndrome and other tampon associated health risks is helpful to avoid any complications with the use of tampons.

For the purposes of the invention as described herein below, hereinafter the materials for use in a tampon can be any of the materials currently used. Furthermore, the construction can be identical to that of the prior art in all components with the exception of how the removal string or cord is assembled to form the tampon of the present invention.

Figure 2:
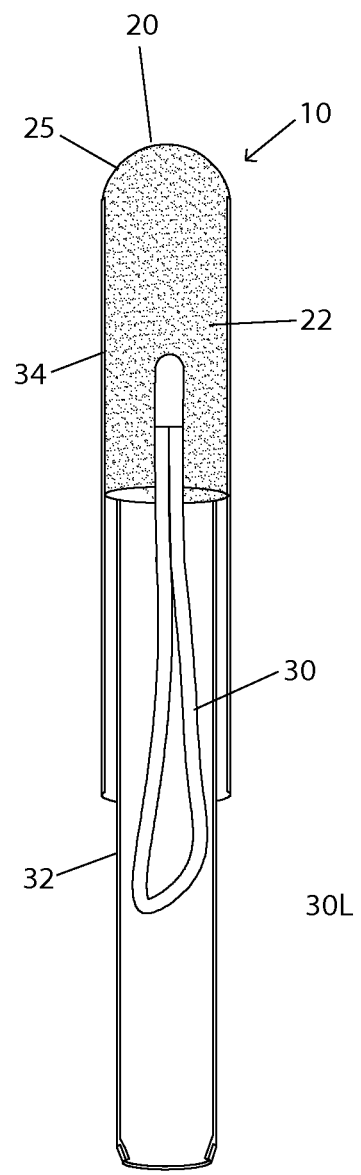
FIG. 2 is a cross sectional view of a tampon assembly with a single looped removal string made according to the present invention.
Figure 3:
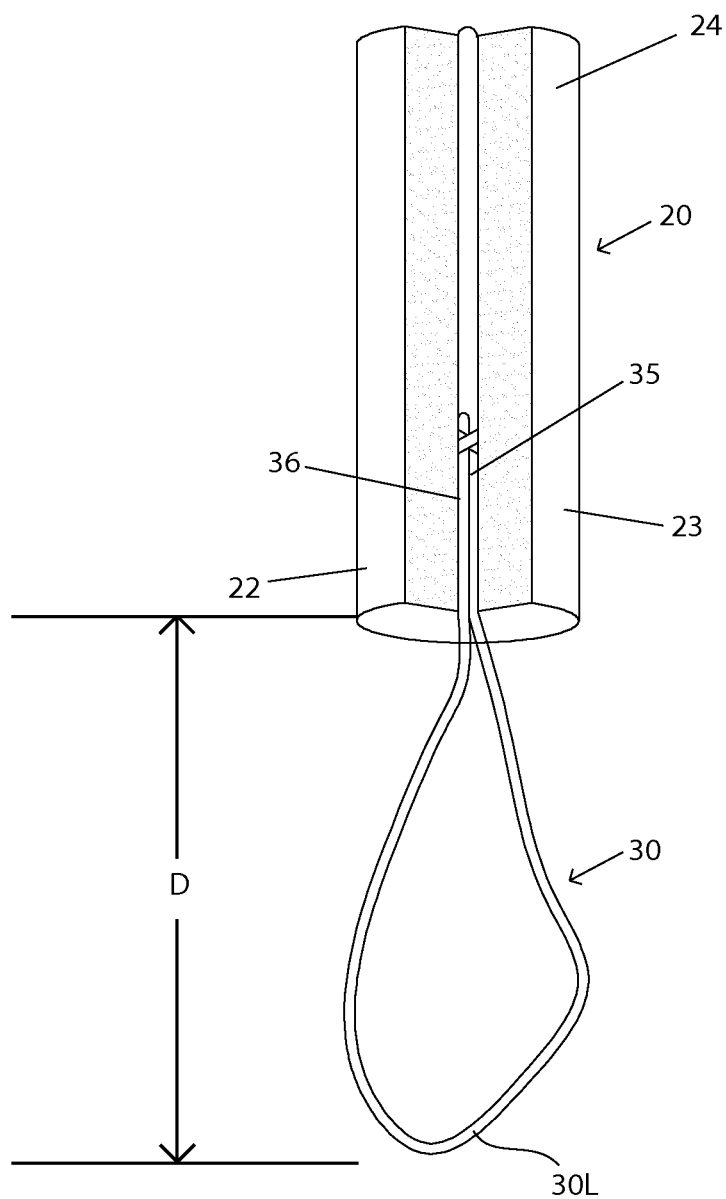
FIG. 3 is a view showing the single looped removal string embedded in a tampon body that has been opened down the longitudinal length of the tampon body to reveal the first and the second ends of the removal string.
Figure 4:
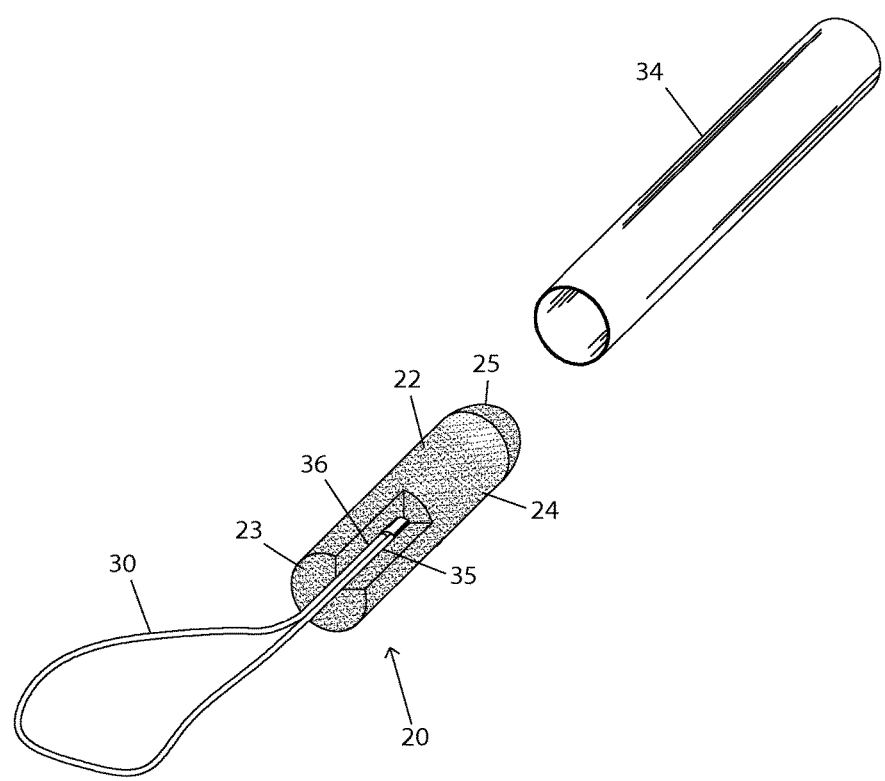
FIG. 4 is an exploded view of the tampon assembly of the present invention.
Figure 4:
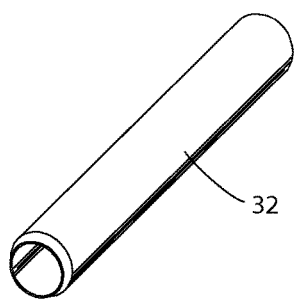

With reference to FIGS. 2, 3 and 4, the tampon assembly 10 of the present invention is illustrated. The tampon assembly 10 as shown in FIG. 2 includes the inner applicator tube 32, the outer applicator tube 34 with the tampon 20 shown housed within the outer applicator tube 34 and extending from the tampon 20 is a removal string 30 that is formed as a single loop 30L. This single loop removal cord can be achieved as shown in FIG. 3 wherein a tampon body 22 can be opened such that is exposes the internal or central portion of the tampon body 22 wherein the ends 35, 36 of the looped tampon removal string 30 are located. The tampon string 30 will have a first end 35 and a second end 36, these ends can be joined or otherwise simply positioned in the area as shown and the tampon folded back on itself to retain the removal string 30. Preferably one or both of the ends 35, 36 are permanently affixed to the inside of the tampon body 22 as illustrated. This affixing of at least one of the ends 35, 36 can be achieved by hot welding the materials together, by adhesively bonding using a glue or other non-toxic material or by sewing the cord or string 30 directly to a portion of the tampon body 22 thereby affixing at least one end 35 such that upon removal the loop 30L can either be maintained if both ends 35, 36 are permanently affixed or alternatively, one end 36 can slip from the tampon body 22 and expose itself such that the string 30 is of the same length as is currently available in the prior art tampons 200. This is achieved by insuring that the one end 36 is releasable from the tampon body 22. While this is an option, it is also important to note that the loop 30L of the removal string 30 can be maintained wherein both ends 35, 36 are permanently affixed and not releasable. In this fashion one simply can grasp the loop 30L with a finger and pull on it to remove the tampon 20 when desired.

FIG. 4 is an exploded view of the tampon assembly 10 of the present invention showing the inner tube 32, the outer tube 34 and the tampon 20 with the single loop 30L removal string 30 as formed. In a preferred embodiment, the tampon body 22 itself can have a distal end 23 that is hydrophobic, in other words it is resistant to water or fluid absorption. Additionally, it is recommended that this string or cord 30 itself be made of a material that is hydrophobic and does not tend to absorb water or fluids. The remaining upper portion 24 of the tampon body 22 can be treated or otherwise made of a material that is hydrophilic with an affinity for absorbing fluids, in that case the hydrophilic material will absorb the blood and fluids within the vagina and serve its useful purpose. While the distal end 23 being resistant to fluid absorption will act as a plug preventing the body fluids from entering into the water should one be swimming and alternatively preventing the water from entering into the vagina when worn. This makes the looped tampon 20 of the present invention ideal for swimming. As can be easily appreciated, the looped 30L removal string 30 only extends a distance D from the distal end 23 of the tampon 20 body. This distance D is half or less than half of the length that would normally be extended from a prior art tampon 200. Tampons are commonly made with a single string although some have been made with two strings tied with a knot. This knot can be provided and tied in such a fashion that it creates the appearance of a loop. The disadvantage of this type of a system is these strings are usually knotted typically in a position that a large amount of strings approximately 4 inches to 6 inches extends from the body 202 of the tampon 200. This creates that unsightly appearance that when a swimmer wears a tampon, the string can extend beyond the bathing suit creating the embarrassing situation knows that the woman is wearing a tampon. This is completely avoided by the present invention in that the small loop 30L itself is contained well within the body cavity such that none of the loop 30L needs to be exposed in any fashion. This greatly facilitates the use of swimsuits, particularly swimsuits that are cut with a reasonably small amount material covering the vaginal area. This insures that the woman can feel comfortable that the string 30 itself will be concealed within the body cavity. Removal is facilitated by the loop 30L because one can simply use a finger to insert and grasp the loop to facilitate removal as previously discussed. With this design, the wearer can feel confident that she can swim without any exposure of the removal string 30. While the activity of swimming is the most common occurrence where the tampon string 30 can be exposed, it is not the only situation that risks of embarrassing string exposure can occur. For example, activities such as tennis, running, modeling, gymnastics, wearing of short shorts, dancing, cheerleading all are situations where the looped tampon 20 of the present invention would add to security and comfort knowing the looped string 30L would never be dangling from the clothing. Furthermore, this avoids the cumbersome requirement of cutting the strings of a conventional or prior art tampon which has its own inherent risk. Such cut strings can be cut so short that they limit the ability to grasp or even find the string once it is inserted into the body cavity. A single string cut provides a limited chance to grasp once inserted; as a result it may require the woman to use forceps or some other device to remove the tampon. This is generally an unacceptable practice, however, the loopon tampon provides a small loop 30L that is easily accessible and provides even a simpler way of removing a tampon because a finger can be slipped directly into the loop 30L and this facilitates pulling the tampon 20 out. There is no risk of being unable to capture a loop 30L as opposed to trying to grasp one end of a cut string. Furthermore, the user does not have to modify the design in any fashion. The looped tampon 20 can be made using any of conventional tampons currently sold.

The improved can be manufactured using a method of manufacturing an improved tampon having the steps of providing a tampon body, attaching a removal string, having a length (L) between a first end and second end permanently affixing at or along at least one first end of the string to the tampon body, and looping the second end back into the tampon body and attaching thereto to form a shortened single loop. The step of affixing the second end includes the step of attaching the second end to the tampon body, the second end is permanently attached or removably attached to the tampon body and the single loop extends a distance D from the tampon body less than half the length (L) of the removal string. The second end can be releasably attached to the tampon body and can be detached from the tampon body to facilitate removal allowing the removal string to be extended to a full removal length. The removal string first and second ends when attached to the tampon body form the single loop in a one piece knotless loop. The step of attaching at least one first end includes one or more steps of sewing, hot welding, bonding, adhesively gluing or otherwise permanently affixing the end to the tampon body. An alternative method of manufacturing an improved tampon has the steps of providing a tampon body, attaching two removal strings to the tampon body, and tying together the unattached ends of the two removal strings to form a single knotted loop.

This knotted loop must be configured to extend similarly a short distance (D) from a tampon body to prevent the removal string tied ends from extending outside the body cavity of the vagina. These and other alternative looped designs of the removal string 30 are considered within the scope of the invention.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

The invention claimed is:

1. An improved tampon comprising:
    a pledget type tampon body having an interior and a distal end, the interior having a central portion;
    a removal string having a first end, a second end, and an intermediate portion extending between the first end and the second end, the first end is permanently affixed to the pledget type tampon body and the second end is releasably attached to the pledget type tampon body thereby forming a loop;
    wherein the removal string extends less than two inches beyond the distal end such that the intermediate portion of the removal string forms a loop that is external to the pledget type tampon body; and
    wherein the pledget type tampon body comprises an upper portion formed of a hydrophilic material for improved blood absorption and a lower portion formed of a water blocking hydrophobic material.

2. The improved tampon of claim 1 wherein the first end is sewn, hot welded, bonded, or adhesively glued to the pledget type tampon body.

3. The improved tampon of claim 1 wherein the removal string is made of a hydrophobic material to prevent water or blood absorption.

4. A tampon comprising:
    a pledget type tampon body having a central portion and a distal end;
    a loop extending from the distal end of the pledget type tampon body, the loop having a first end and a second end, the first end is permanently affixed to the central portion of the pledget type tampon body to anchor the loop to the pledget type tampon body, the second end is releasably affixed to the distal end of the pledget type tampon body such that it can be detached from the pledget type tampon body to facilitate removal, the pledget type tampon body folded to anchor the first end and the second end within the central portion of the pledget type tampon body;
    wherein the loop exits the pledget type tampon body at a single location of the distal end and extends less than two inches beyond the distal end external to the pledget type tampon body;
    wherein the loop facilitates removal of the pledget type tampon body from a cavity of a user; and
    wherein the pledget type tampon body comprises an upper portion formed of a hydrophilic material for improved blood absorption and a lower portion formed of a water blocking hydrophobic material.

5. The tampon of claim 4 wherein the first end is sewn, hot welded, bonded, or adhesively glued to the pledget type tampon body.

6. The tampon of claim 4 wherein the loop is made of a hydrophobic material to prevent water or blood absorption.

* * * * *